(12) United States Patent
Tepper

(10) Patent No.: US 6,371,973 B1
(45) Date of Patent: Apr. 16, 2002

(54) FORCEPS USEFUL FOR INTRABODY GUIDING AND/OR POSITIONING OF A MEDICAL INSTRUMENT

(75) Inventor: Ronnie Tepper, Herzelia (IL)

(73) Assignee: Ron-Tech Medical Ltd., Kfar Saba (IL)

( * ) Notice: Subject to any disclaimer, the term of this patent is extended or adjusted under 35 U.S.C. 154(b) by 0 days.

(21) Appl. No.: 09/490,456

(22) Filed: Jan. 24, 2000

Related U.S. Application Data

(63) Continuation-in-part of application No. 09/368,175, filed on Aug. 4, 1999, now Pat. No. 6,210,330.

(51) Int. Cl.$^7$ .............................. A61B 17/28; A61B 8/00
(52) U.S. Cl. ........................................ 606/205; 600/439
(58) Field of Search .................................. 606/205, 206, 606/207, 208, 209, 210, 135, 42, 119, 108; 600/206, 461, 407, 443, 437, 439; 604/104, 105, 106

(56) References Cited

U.S. PATENT DOCUMENTS

| | | | | |
|---|---|---|---|---|
| 1,193,988 A | * | 8/1916 | Burdin | 606/205 |
| 3,083,711 A | * | 4/1963 | Ramsay | 606/201 |
| 5,643,316 A | * | 7/1997 | Kaiser et al. | 606/205 |
| 6,210,330 B1 | * | 4/2001 | Tepper | 600/439 |

* cited by examiner

*Primary Examiner*—David O. Reip
*Assistant Examiner*—Vy Q. Bui

(57) ABSTRACT

A forceps useful in intrabody positioning of a medical instrument or a device. The forceps comprises (a) a first arm including a first finger holding portion, a first pivot portion and a first tissue holding portion; and (b) a second arm including a second finger holding portion, a second pivot portion and a second tissue holding portion; wherein the first pivot portion is attached to the second pivot portion so as to form a pivot point about which the first and the second arms co-rotate in a scissor-like motion from a grasping position to an open position and wise versa, whereas the first and the second finger holding portions are positioned on one side of a plane defined by a length of the first arm, the plane is perpendicular to the scissor-like motion.

27 Claims, 9 Drawing Sheets

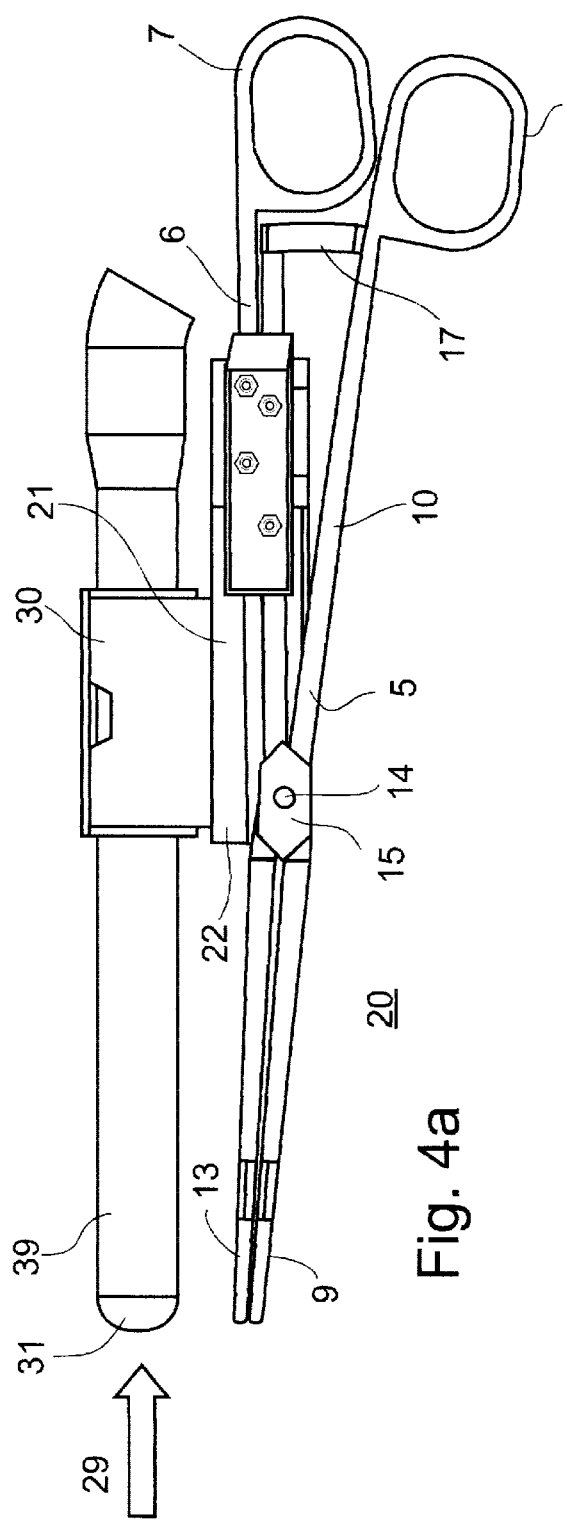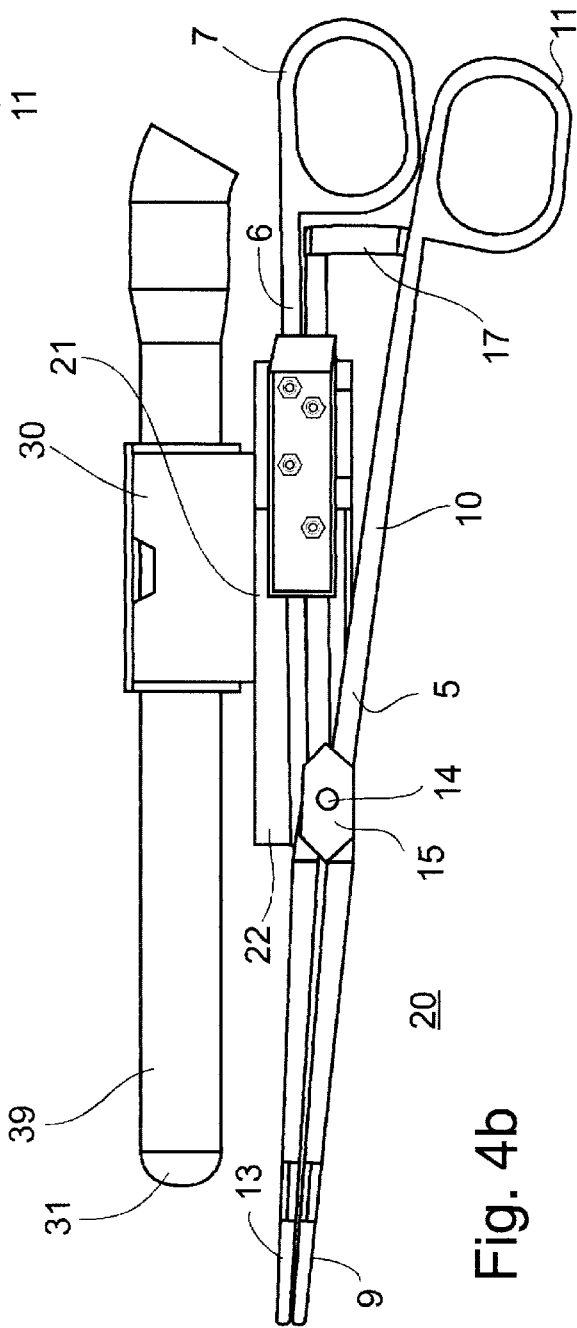
Fig. 4a
Fig. 4b

FORCEPS USEFUL FOR INTRABODY GUIDING AND/OR POSITIONING OF A MEDICAL INSTRUMENT

RELATED APPLICATION

The present application is a Continuation-in-Part of U.S. application Ser. No. 09/368,175, filed Aug. 4, 1999, now U.S. Pat. No. 6,210,330 on Apr. 3, 2001.

FIELD AND BACKGROUND OF THE INVENTION

The present invention relates to forceps which are asymmetric along the length thereof and as such can be attached to various medical instruments so as to enable positioning and/or anchoring of said instruments within the body. More particularly, the present invention relates to a forceps which is attachable to an endovaginal ultrasound transducer and which is utilizable for positioning and/or anchoring said ultrasound transducer against the cervix.

The use of manipulative instruments in the course of examination of a patient, or in the course of a surgical procedure, are well known in the art.

Various forceps and retention devices have been developed which, in one way or another, conform to the physiology of a person. Specific amongst these prior art devices are retention, seizing and holding tools and forceps conformed for particular aspects of the patient's anatomy.

Amongst these are tenaculums which also serve as uterine cervical holders and as such are conformed or adapted for intra-vaginal use. Such cervical holders can be utilized, for example, to position endovaginal ultrasound transducers against the uterine cervix so as to enable monitoring obstetric and gynecological procedures.

For example, WO 99/03399 describes an apparatus which includes a cervical holder for holding the patient's cervix and an attached connector for interconnecting an ultrasound transducer to the cervical holder. The apparatus described in WO 99/03399 can be used to guide and monitor, in real time, intra uterine, cervical and tubal procedures such as, for example, curettage or evacuation of the uterine cavity for diagnostic and/or therapeutic purposes, and the like.

Although this apparatus provides several advantages over similar prior art devices, which advantages significantly improve the precision with which an intra uterine, cervical and tubal procedures can be performed, several limitations are still inherent to this apparatus, which limitations, in part, arise from the configuration of the cervical holder utilized thereby.

As is shown in FIGS. 1a–b, when in use, the apparatus described in WO 99/03399, is positioned within the vagina and is attached via a cervical holder or grasper onto cervical tissue, as is shown by arrow A. As a result, the ultrasound transducer, connected thereto, contacts a tissue region adjacent to the site of attachment, as shown by arrow B.

Since the finger holding portions (arrow C) of the cervical holder are positioned such that the transducer cannot be positioned directly over the cervical holder, shifting of the transducer to the side of the cervical holder is necessary. This severely limits the accuracy with which the transducer assembly is positioned since such an assembly is oftentimes placed blindly and offline, and as such a physician relies on the cervical holder to guide the transducer to the desired position. Thus, when the cervical holder and the transducer are not in the same plane, the chances or inaccurate positioning or orientation are increased. In addition, this configuration of the finger holding portions severely limits the accessibility of these portions, since they are partially blocked by the transducer, thus severely limiting the ability of a physician to operate such a cervical holder while positioning the transducer.

There is thus a widely recognized need for, and it would be highly advantageous to have, forceps which can be used to guide and anchor in position an intrabody medical instrument such as endovaginal ultrasound transducer devoid of the above limitations.

SUMMARY OF THE INVENTION

According to one aspect of the present invention there is provided a forceps useful in intrabody or surface positioning of a medical instrument or a device, the forceps comprising (a) a first arm including a first finger holding portion, a first pivot portion and a first tissue holding portion; and (b) a second arm including a second finger holding portion, a second pivot portion and a second tissue holding portion; wherein the first pivot portion is attached to the second pivot portion so as to form a pivot point about which the first and the second arms co-rotate in a scissor-like motion from a grasping position to an open position and wise versa, whereas the first and the second finger holding portions are positioned on one side of a plane defined by a length of the first arm, the plane is perpendicular to the scissor-like motion.

According to further features of the invention, in the grasping position of the forceps, (i) the tissue holding portion of the second arm on one side of the pivot point is substantially parallel to the tissue holding portion of the first arm on the corresponding side of the pivot point; (ii) the finger holding portion of the second arm on the other side of the pivot point forms an obtuse angle with respect to the tissue holding portion of the second arm; and (iii) the finger holding portions of the first and second arms terminate in finger-receiving elements which are both located on one side of the first arm and are aligned with each other in the direction of the scissor-like motion.

According to another aspect of the present invention there is provided an apparatus for guidance and monitoring of intra-uterine, cervical and tubal procedures, the apparatus comprising an assembly, including (a) an endovaginal ultrasound transducer being adapted for insertion into a portion of a patient's vagina so as to be positionable against a cervix of the patient; (b) a forceps including (i) a first arm including a first finger holding portion, a first pivot portion and a first tissue holding portion; and (ii) a second arm including a second finger holding portion, a second pivot portion and a second tissue holding portion; wherein the first pivot portion is attached to the second pivot portion so as to form a pivot point about which the first and the second arms co-rotate in a scissor-like motion from a grasping position to an open position and wise versa, whereas the first and the second finger holding portions are positioned on one side of a plane defined by a length of the first arm, the plane is perpendicular to the scissor-like motion; and (c) a connector for interconnecting the ultrasound transducer and the forceps, the connector being constructed so as to enable counter resisted movement of the ultrasound transducer relative to the forceps, the counter resisted movement being in a direction away from the cervix.

According to yet another aspect of the present invention there is provided a system for guidance and monitoring of a medical instrument utilized in intra-uterine, cervical and tubal procedures, the system comprising (a) an endovaginal ultrasound transducer being adapted for insertion into a portion of a patient's vagina; (b) a forceps including (i) a first arm including a first finger holding portion, a first pivot portion and a first tissue holding portion; and (ii) a second arm including a second finger holding portion, a second pivot portion and a second tissue holding portion; wherein the first pivot portion is attached to the second pivot portion so as to form a pivot point about which the first and the second arms co-rotate in a scissor-like motion from a grasping position to an open position and wise versa, whereas the first and the second finger holding portions are positioned on one side of a plane defined by a length of the first arm, the plane is perpendicular to the scissor-like motion; (c) a connector for interconnecting the ultrasound transducer and the forceps, the connector being constructed so as to enable counter resisted movement of the ultrasound transducer relative to the forceps, the movement being in a direction away from the cervix of the patient; and (d) a device for monitoring an alignment of a medical instrument with respect to an ultrasonic beam produced by the endovaginal ultrasound transducer.

According to still further features in the described preferred embodiments the first and the second tissue holding portions are adapted for grasping a cervical tissue.

According to still further features in the described preferred embodiments the connector includes (i) a forceps portion being attachable to the forceps; and (ii) an ultrasound holder portion being attachable to the forceps portion, the ultrasound holder portion including a body and an ultrasound acceptor being for holding the ultrasound transducer, the acceptor is connected to the body in a manner so as to allow counter resisted movement of the acceptor relative to the body along a longitudinal axis of the ultrasound transducer.

According to still further features in the described preferred embodiments the ultrasound holder portion further includes a spring element interposed between the acceptor and the body such that the counter resisted movement of the acceptor relative to the body in a direction opposite to the patients cervix is counter resisted by the spring element.

According to still further features in the described preferred embodiments the ultrasound holder portion further includes an ultrasound adapter element positioned within the acceptor for firmly holding the ultrasound transducer within the acceptor.

According to still further features in the described preferred embodiments the ultrasound holder portion of the connector is constructed so as to detach from the forceps portion upon an application of a force of a predetermined magnitude to the endovaginal ultrasound transducer along a longitudinal axis thereof.

According to still further features in the described preferred embodiments the forceps includes an element attached to, or integrally formed with the first arm, the element being for engaging the forceps portion of the connector.

According to still further features in the described preferred embodiments the device includes an extension coaxially connected at a distal end of the endovaginal ultrasound transducer thereby facilitating visual alignment of the medical instrument with respect to the endovaginal ultrasound transducer and therefore also with respect to the ultrasonic beam.

According to still further features in the described preferred embodiments the device includes at least one light beam generator connected either to the connector, to the ultrasound transducer or to the forceps, the light beam generator being for generating at least one light beam substantially in a plane defined by the ultrasound beam, the at least one light beam, when impinges on the medical instrument serves for facilitating visual alignment of the medical instrument with respect to the endovaginal ultrasound transducer and therefore also with respect to the ultrasound beam.

According to still further features in the described preferred embodiments the device is an imaging device connected to the endovaginal ultrasound transducer, the imaging device being for generating an image of the medical instrument superimposable on a plane defined by the ultrasound beam, thereby facilitating alignment of the medical instrument with respect to the endovaginal ultrasound transducer and therefore also with respect to the ultrasound beam.

According to still further features in the described preferred embodiments the image is displayed on a screen.

According to still further features in the described preferred embodiments the imaging device includes a camera.

According to still further features in the described preferred embodiments the camera is sensitive to light in the visible range.

According to still further features in the described preferred embodiments the camera is an infrared camera.

According to still further features in the described preferred embodiments the imaging device includes an ultrasound generator.

According to still further features in the described preferred embodiments the medical instrument is provided with marks along at least a portion thereof, the marks are identifiable by the imaging device and are therefore usable for image recognition analysis.

According to still further features in the described preferred embodiments the device includes at least two electromagnetic field generators for generating electromagnetic fields, one of the electromagnetic field generator is connected either to the connector, to the ultrasound transducer or to the forceps, whereas the other electromagnetic field generator is connected to the medical instrument, the device further includes at least one electromagnetic field sensor of a predetermined position, such that by analyzing magnetic fields perceived by the at least one electromagnetic sensor, spatial information of the relative locations of the electromagnetic field generators and therefore of the endovaginal ultrasound transducer and the medical instrument is obtainable, thereby facilitating alignment of the medical instrument with respect to the ultrasound beam.

According to still further features in the described preferred embodiments the medical instrument is selected from the group consisting of an image transmitting device and a surgical instrument.

The present invention successfully addresses the shortcomings of the presently known configurations by providing a forceps utilizable in positioning and/or anchoring of a medical device or instrument attached thereto, such as, for example, an intra-vaginal ultrasound transducer.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 4a–b are side views of an apparatus for guiding and monitoring an intra-uterine procedure according to the present invention showing a longitudinal displacement of the ultrasound transducer as a response to a force applied to a proximal end thereof.

DESCRIPTION OF THE PREFERRED EMBODIMENTS

Figure 1A:
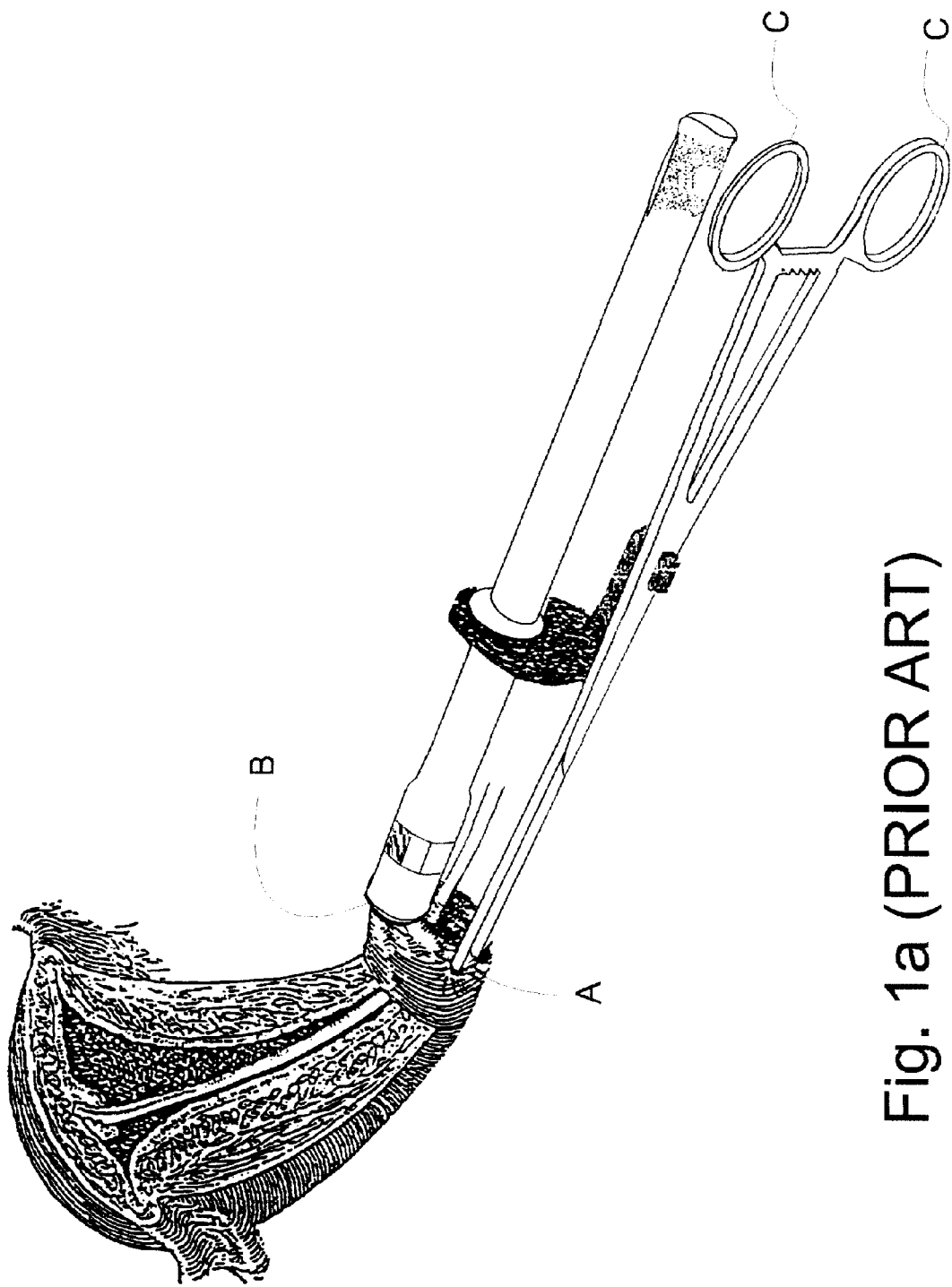
FIGS. 1a–b are drawings depicting a prior art apparatus for guiding and monitoring an intra-uterine procedure illustrating the positioning of such an apparatus relative to a cervix as shown either in a perspective view (FIG. 1a) or a side view (FIG. 1b)
Figure 1B:
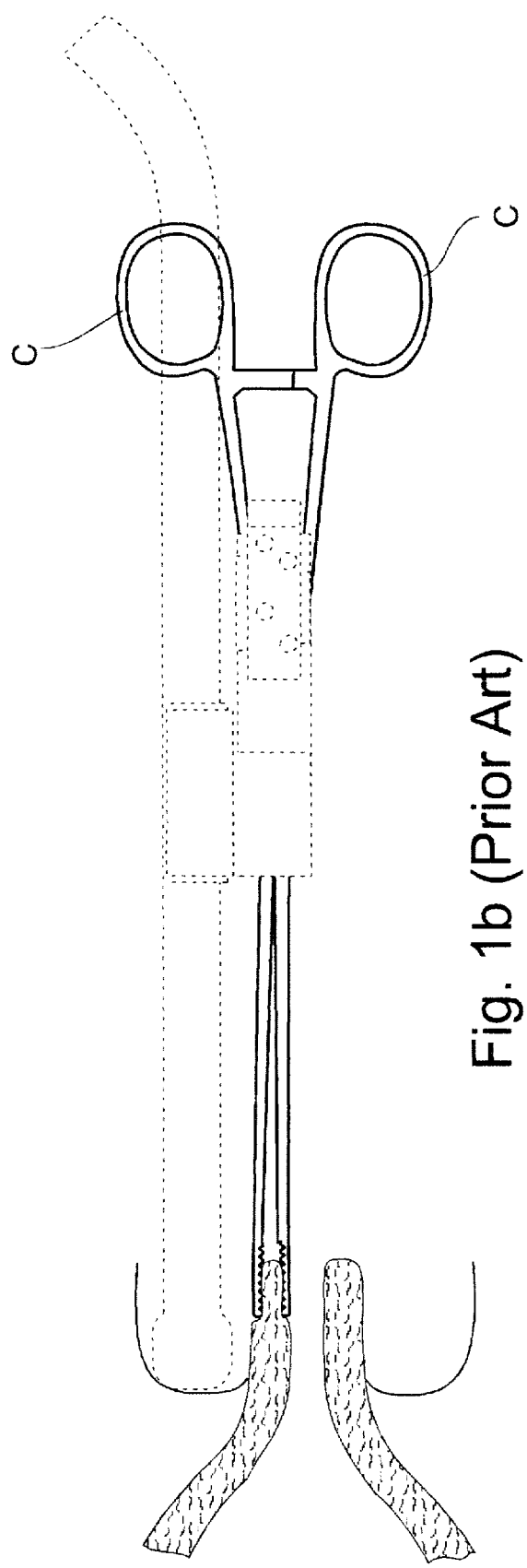
Figure 2:
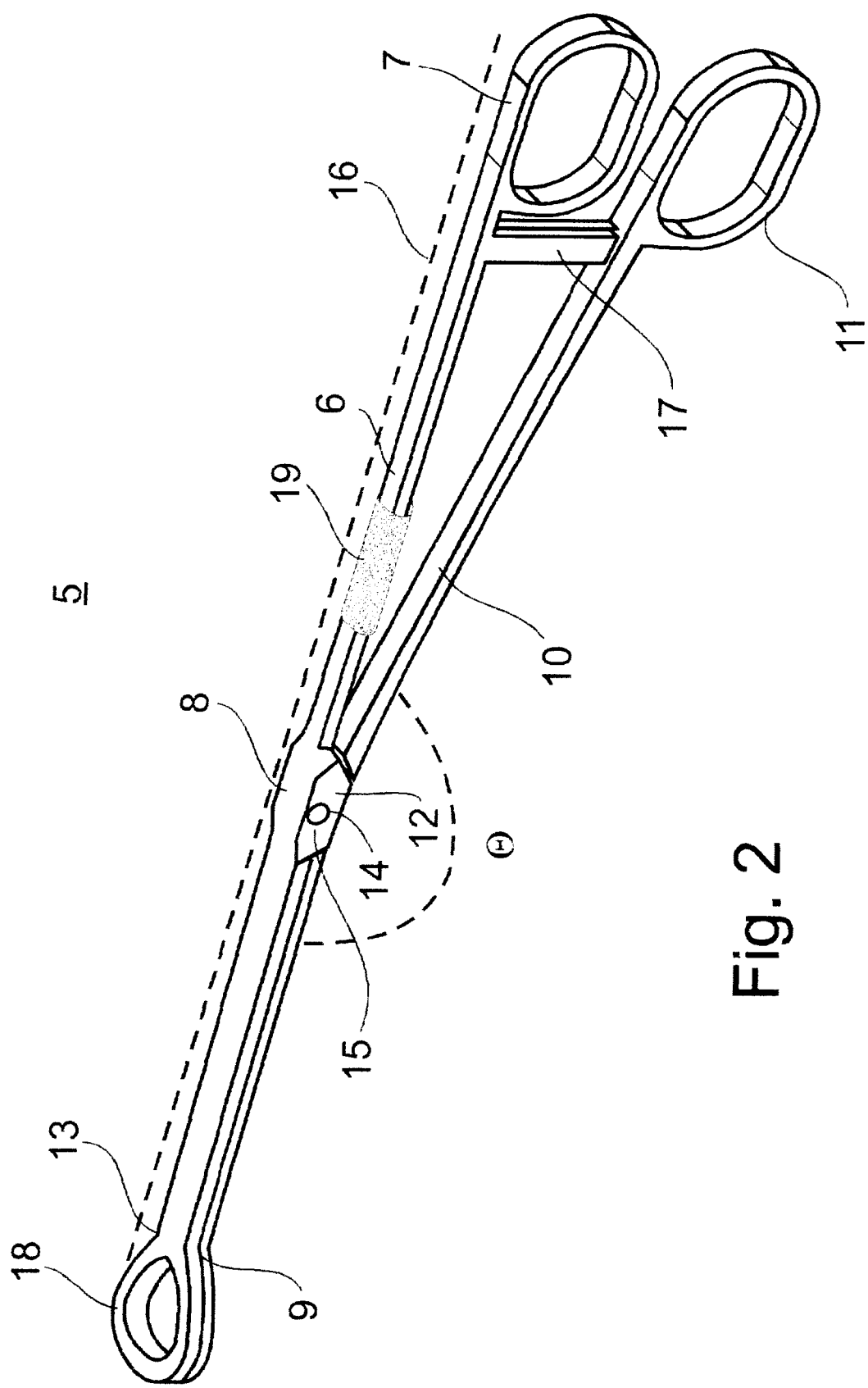
FIG. 2 is a perspective view of a forceps according to the present invention.

The present invention is of a forceps which can be utilized for intrabody positioning of a medical instrument or device. Specifically, the present invention can be used to position an intra-vaginal ultrasound transducer. Using appropriate imaging software and hardware, an ultrasound transducer according to the present invention can be used to generate either a two or a three dimentional ultrasound image.

The principles and operation of a forceps according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein the term "forceps" refers to an instrument for seizing or grasping a tissue structure for the purpose of compression or traction. As such, the term forceps also refers to clamps, tenacula and any other medical instrument of this type which is manually operated and capable of gasping a tissue structure.

As further used herein, the terms "proximal" and "proximally" refer to the position of tissue holding portions of a forceps, while the terms "distal" and "distally" refer to a position of finger holding portions of the forceps of the present invention.

Referring now to the drawings, FIGS. 2 and 4–8 illustrate the forceps according to the present invention which is referred to hereinunder as forceps 5.

Forceps 5 includes a first arm 6, which includes a first finger holding portion 7, a first pivot portion 8 and a first tissue holding portion 9. Forceps 5 further includes a second arm 10 which includes a second finger holding portion 11, a second pivot portion 12 and a second tissue holding portion 13.

First pivot portion 8 is attached via a screw, a pin or the like, as is indicated by 14, to second pivot portion 12 so as to form a pivot point 15, about which arms 6 and 10 co-rotate in a scissor-like motion from a grasping position to a non-grasping (open) position, and vice versa. Thus, in order to open forceps 5, finger holding portions 7 and 11 are pulled apart and vice a versa. When forceps 5 is in a grasping position, tissue holding portions 9 and 13 are biased one against the other so as to form a clamping or grasping area 18 which can be used to clamp forceps 5 to a tissue. It will be appreciated that clamping area 18 can be of any configuration known in the art including, but not limited to, Ovum Forceps produced by, for example, Heywood-Smith; Kelly; Noto; Aesculap Ltd.

In addition, when forceps 5 is in its grasping position, finger holding portions 7 and 11 are positioned on one side of a plane (indicated by 16), which plane is defined by the length of arm 6 and is orthogonal to the scissor-like motion. As a result, and in sharp distinction to prior art forceps, forceps 5 is asymmetrical.

As is further detailed hereinunder, the latter feature of forceps 5 is particularly advantageous when forceps 5 is utilized for the intrabody positioning of a medical instrument or device.

Forceps 5 also preferably includes a locking element 17 which inter-locks arms 6 and 10 when forceps 5 is in its grasping position.

To achieve an asymmetric configuration wherein both finger holding portions 7 and 11 are positioned on one side of plane 16, arm 10 is preferably formed with an angle (indicated by θ) around pivot point 15, wherein arm 6 follows plane 16. This configuration allows finger holding portions 7 and 11 to be positioned one above the other and yet allows both to be positioned on one side of plane 16.

Alternatively, the portion spanning from finger holding portion 11 to pivot portion 12 can be configured shorter in arm 10 as is compared to arm 6. In this case, arm 10 also follows plane 16 but finger holding portion 11 is positioned proximally to finger holding portion 7, thus creating a staggered configuration for finger holding portions 7 and 11.

It will thus be seen that, in the grasping position of the forceps, (i) the tissue holding portion 13 of arm 10 on one side of the pivot point 15 is substantially parallel to the tissue holding portion 9 of arm 6 on the corresponding side of the pivot point; (ii) the finger holding portion 11 of arm 10 on the other side of the pivot point 15 forms an obtuse angle with respect to the tissue holding portion 13 of arm 10; and (iii) the finger holding portion 7 of arm 6 and the finger holding portion 11 of arm 10 terminate in finger-receiving elements (shown as loops) which are both located on one side of arm 6 and are aligned with each other in the direction of the scissor-like motion produced when grasping or releasing tissue between the two tissue holding portions 13 and 9.

Thus, according to a preferred embodiment of the present invention and as specifically shown in FIGS. 4a–8 forceps 5 forms a part of an apparatus 20 which further includes an intra-vaginal ultrasound transducer and which is utilizable for guiding and monitoring an intra-uterine procedure. Such a procedure can include, but is not limited to, (i) curettage or evacuation of the uterine cavity for diagnostic and/or therapeutic purposes; (ii) removal of an endometrial polyp, submucous myoma or other tissue; (iii) introduction or extraction of an intra-uterine contraceptive device (IUCD) and other foreign bodies; (iv) systematic sampling of the endometrium and/or the endocervix for diagnostic purposes; (v) embryo transfer into the endometrial cavity; (vi) embryo transfer into the fallopian tube; (vii) fallopian tube canullation; (viii) ultrasound guided fetal reduction; (ix) simultaneous insertion of an image transmitting device such as endoscopy equipment into the uterine cavity for complementary diagnostic and/or therapeutic purposes; (x) chorionic villi sampling; (xi) fetoscopy; (xii) amniocentesis; (xiii) fetal tissue sampling (xiv) feticid and (xv) hydrosonography with saline or contrast agents.

To enable attachment of forceps 5 to an ultrasound transducer to thereby form apparatus 20, forceps 5 preferably includes an element 19 attached to, or integrally formed with arm 6. Element 19 serves for engaging forceps 5 via a connector to an intra-vaginal ultrasound transducer, although as further detailed hereinbelow other configurations of attachment can be realized by the present invention.

FIG. 3–8 depict a connector 21 useful for attaching forceps 5 to an intra-vaginal ultrasound transducer.

Figure 3:
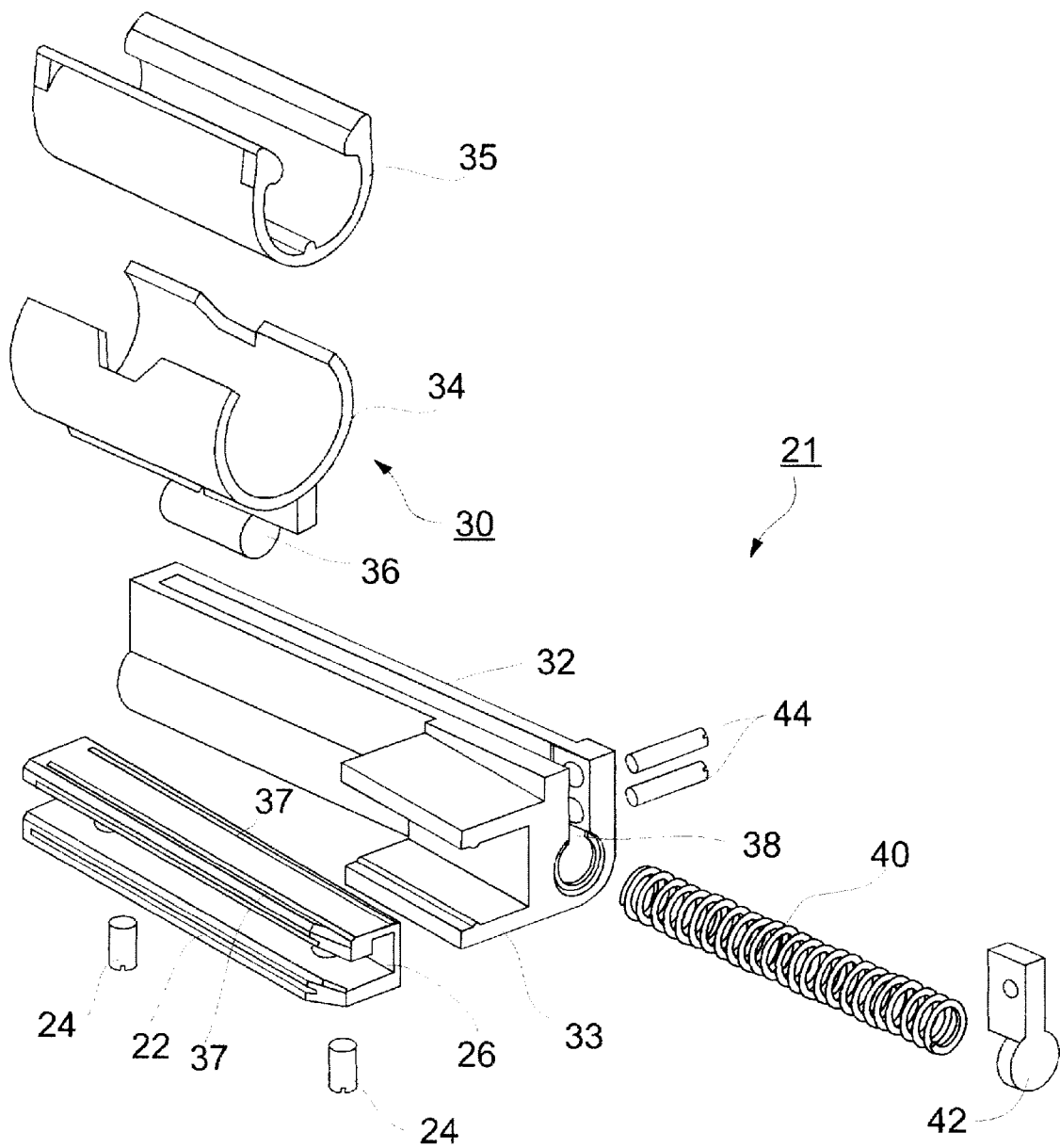
FIG. 3 is an exploded view of cervical and ultrasound holder portions of an apparatus for guiding and monitoring an intra-uterine procedure according to the present invention.

As specifically shown in FIG. 3, and according to a preferred embodiment of the present invention, connector 21 includes a forceps holder portion 22 which is attachable to forceps 5. Alternatively, portion 22 can be integrally formed with arm 6 of forceps 5. According to one configuration, forceps portion 22 is attached to forceps 5 via a groove 26. Groove 26 tightly engages element 19 via screws 24 which thread through forceps portion 22 and contact arm 6 of forceps 5. In this configuration, forceps portion 22 is reversibly attachable to element 19 of forceps 5.

Connector 21 also includes an ultrasound holder portion 30 which attaches to forceps portion 22. This attachment can be provided by clamping or sliding a U-shaped clasp 33 over grooves 37 provided on forceps portion 22.

As specifically shown in FIG. 3, ultrasound holder portion 30 includes a body 32 and an ultrasound acceptor 34 which serves for holding an ultrasound transducer 39 (shown in FIGS. 4a–8).

According to a preferred embodiment of the present invention, ultrasound holder portion 30 further includes an ultrasound adapter element 35 positioned within acceptor 34 for firmly holding ultrasound transducer 39 within acceptor 34. It will be appreciated that adapter element 35 can be configured in a variety of sizes and shapes so as to accommodate a variety of ultrasound transducers 12 having different sizes.

It will be appreciated that ultrasound holder portion 30 and forceps portion 22 can be manufactured from a variety of materials such as, but not limited to, plastics, metals and composite materials. Portions 30 and 22 can be fabricated via injection molding, CNC and the like and can be either disposable or reusable in which case portions 30 and 22 are fabricated out of autoclavable materials.

According to a preferred embodiment of the present invention connector 21 is constructed so as to enable counter resisted movement of ultrasound transducer 39 relative to forceps 5.

Thus, as shown by FIG. 3 and according to a preferred embodiment of the present invention, acceptor 34 is connected to body 32 in a manner so as to allow counter resisted movement of acceptor 34 relative to body 32 along a longitudinal axis of apparatus 20. This is achieved by providing acceptor 34 with a tongue element 36, which fits within a slot 38 formed in body 32. This configuration allows movement of acceptor 34 relative to body 32 along a longitudinal axis of body 32 and therefore along a longitudinal axis of connector 21. To counter resist this movement, ultrasound holder portion 30 is provided with a spring element 40 positioned within slot 38. Spring element 40 is retained within slot 38 via a stoppage 42 and pins 44. Thus, movement of acceptor 34 in a direction away from the cervix of a patient, when apparatus 20 is utilized, is counter resisted by spring element 40. Although spring element 40 is depicted in FIG. 3 as a coil spring, any element with elastic properties can be utilized by apparatus 20 of the present invention, examples include, but not limited to elastomers.

As specifically shown in FIGS. 4a and 4b when a force, as indicated by arrow 29, is applied to a proximal end 31 of ultrasound transducer 39, ultrasound transducer 39 moves in a direction away from the cervix of the patient substantially along a longitudinal axis thereof. Force 29 is a counter force generated when proximal end 31 of transducer 39 is forced against a cervical or endovaginal tissue region of the patient. As described above, connector 21 is configured such that this movement is counter resisted by a counter force which serves as a returning force. As a result, proximal end 31 of ultrasound transducer 39 maintains contact with a cervical or endovaginal tissue region of the patient when apparatus 20 is utilized. This contact is also maintained during a procedure as a result of physician manipulation or patient movements.

According to another preferred embodiment of the present invention ultrasound portion 30 of connector 21 is preferably constructed so as to enable the detachment of an ultrasound transducer from forceps portion 22 upon an application of a force of a predetermined magnitude to a proximal end of the ultrasound transducer along a longitudinal axis thereof. For example if force 29 exceeds a force which can be countered by spring element 40 and which can lead to tissue damage at the site of contact between transducer 39 and a cervical or endovaginal tissue region, the connection between forceps holder 22 and ultrasound portion 30 disintegrates. This feature of connector 21 also prevents damage to cervical tissue held by holders 9 and 13 of forceps 5, since excessive force in the direction of the cervix can lead to an excessive pulling force on the adjacent tissue by forceps 5.

It will be appreciated that the above described configuration is one configuration of connector 21 with which counter resisted movement of ultrasound transducer 39 relative to forceps 5 can be realized. Alternative configurations employing spring elements at a point of attachment between ultrasound holder portion 30 and forceps portion 22, or alternatively between forceps portion 22 and arm 6 of forceps 5 can also be realized and utilized by apparatus 20 of the present invention.

It will be appreciated that maintaining contact during a procedure is imperative for optimal ultrasound resolution since ultrasound beams require the presence of a water medium, such as biological tissue, to appropriately propagate.

Furthermore, the design described herein with respect to connector 21 provides an additional advantage as is compared with the connector of WO 99/03399. Since holders 9 and 13 serve as a fulcrum point, should excess force be applied via end 31 of transducer 39 onto the cervix tissue, transducer 39 is reverse translated so as to reduce the force applied thereby onto the tissue and prevent damage.

According to another aspect of the present invention, apparatus 20 is utilized to monitor a variety of intra-uterine, cervical or tubal procedures.

Thus, monitoring of such procedures is effected by the following method steps in which, in a first step, apparatus 20 is assembled by connecting ultrasound holder portion 30 to element 22 which is attached to, or integrally formed with, forceps 5. Following this step, ultrasound transducer 39 is attached to acceptor 34 via adapter 35, and it is appropriately positioned. Apparatus 20 is then inserted into the patients vaginal cavity and ultrasound transducer 39 is positioned against the patient's endovaginal or cervical tissue region and forceps 5 is then used to grip an adjacent cervical or endovaginal tissue region of a patient by means of holders 9 and 13. Alternatively holder portions 30 and 22 are assembled, inserted and positioned within the vagina of a patient via forceps 5, following which ultrasound transducer 39 is attached to holder 30 and is appropriately positioned.

During an intrauterine procedure, apparatus 20 is preferably held by one hand of the physician via forceps 5, so that the other hand is free to conduct the procedure. Since the diameter of ultrasound transducer 10 is substantially small, the physician may conveniently introduce a medical instrument through the cervix of the patient into the uterine cavity. The surgical procedure is then carried out and is continuously guided and monitored by means of ultrasound transducer 39.

It will further be appreciated in this case that since forceps 5 of the present invention is configured such that holds 7 and 11 are directly below ultrasound transducer 39, a physician can easily manipulate forceps 5 into position even in a small confined space and in addition be provided with ample space between apparatus 20 and the vaginal wall through which a medical instrument can be introduced into the uterine cavity. Furthermore, since both forceps 5 and transducer 39 are co-aligned with plane 16 a more accurate positioning of proximal end 31 of transducer 39 can be effected by forceps 5 as compared to assemblies employing prior art forceps or cervical holders.

It will be appreciated by one ordinarily skilled in the art that guiding a medical instrument is used herein as a non limiting example for guiding any medical instrument (tool) for diagnostic and/or surgical purposes into the cervix, uterine or fallopian tubes of the patient. Such instruments include, but are not limited to, uterine sound—plastic disposable or stainless steel, uterine dilators—hegar double or single end, uterine curettes, uterine dressing, hysterectomy forceps, ovum forceps, intra-uterine device remover, biopsy punches, endocervical speculum, aspirate curette, vacuum curette, aspirate tube, coagulator, embryo transfer set, insemination device, embryo gamete intra-fallopian transfer (GIFT) catheter, embryo intra uterine insemination (IUI) catheter, Karman catheter for uterine aspiration, minimally invasive surgery equipment, such as, grasping forceps, scissors, light dissecting/grasping forceps, diathermy balloon intra cavitary, IUCD, hysterosalpingography catheter, uterine catheter, tubal catheter, brush cytology, cervical adapter for hydrotubation, uterine controlling instruments, vacuum intrauterine sound, uterine elevator, Spackmann cannula, Scott uterine manipulator, Hulka controlling tenaculum or forceps, rocket vacuum aspirator curette, uterine depth probe, sampling devices, NOVAK, KEVORKIAN, EXPORA and Pipelle.

It will be appreciated that since the above listed medical instruments are typically operated by the strong (i.e., skilled) hand of the physician, apparatus 20 is held and operated by the weak hand thereof. As such, apparatus 20 is preferably constructed of a light material such that it can be easily held in place and maneuvered by the physician.

According to another aspect of the present invention apparatus 20 is used in combination with an image transmitting device included within a system for guidance and monitoring of a medical instrument utilized in intra-uterine, cervical and tubal procedures.

The image transmitting device may be, for example, an optic fiber, or endoscopy equipment. The image transmitting device may include an image transmitting element such as a CCD or a video camera. The image transmitting device is preferably connected to apparatus 20, such that ultrasound transducer 39 is preferably inserted into the patient's vagina and the image transmitting device is preferably inserted through the cervical canal into the uterine cavity.

For example, transducer 39 may be connected to an endoscopy equipment so as to allow simultaneous monitoring of the surgical procedure by means of two complementary methods, thereby enabling to accurately determine the position of a medical instrument with relation to the uterine wall.

The system described hereinabove not only allows for ultrasonic view of the treated area in the cervix, uterine or fallopian tube, it further allows for ultrasonic view of the operating medical instrument. This can be effected by this system provided that the medical instrument is brought "inside" or "into" the beam generated by the ultrasound transducer, which beam is shaped as a triangle located within the ultrasound plane of view.

Since apparatus 20 is inserted into a portion of the vagina of the patient prior to the insertion of a medical instrument through the cervix, and further since the medical instrument and apparatus 20 are each held by a different hand of the surgeon, an unskilled physician may find it difficult to bring the medical instrument "inside" or "into" the sonography beam.

As further detailed hereinunder, the following embodiments the present invention specifically address this problem.

With reference now to FIGS. 5–8, presented is a system for guidance and monitoring of intra-uterine, cervical and tubal procedures, which is referred to hereinbelow as system 50.

System 50 includes apparatus 20 for generating an ultrasound beam from ultrasound transducer 39 included within apparatus 20 as further described hereinabove with respect to FIGS. 3–4*b*.

System 50 further includes a medical instrument 60. Instrument 60 serves to perform the intra-uterine, cervical or tubal procedure and is typically operable by a strong hand of the surgeon. Medical instrument 60 may be a diagnostic instrument, such as, but not limited to, hysterosalpingography catheter, uterine catheter, tubal catheter, brush cytology, cervical adapter for hydrotubation, uterine controlling instruments, vacuum intrauterine sound, uterine elevator, Spackmann cannula, Scott uterine manipulator, Hulka controlling tenaculum or forceps, rocket vacuum aspirator curette, uterine depth probe, sampling devices, NOVAK, KEVORKIAN, EXPORA and Pipelle, or a surgical instrument, such as, but not limited to, uterine sound—plastic disposable or stainless steel, uterine dilators—hegar double or single end, uterine curettes, uterine dressing, hysterectomy forceps, ovum forceps, intra-uterine device remover, biopsy punches, endocervical speculum, aspirate curette, vacuum curette, aspirate tube, coagulator, embryo transfer set, insemination device, embryo gamete intra-fallopian transfer (GIFT) catheter, embryo intra uterine insemination (IUI) catheter, Karman catheter for uterine aspiration, minimally invasive surgery equipment, such as, grasping forceps, scissors, light dissecting/grasping forceps, diathermy balloon intra cavitary and IUCD.

System 50 further includes a device 62 which serves for monitoring the alignment of medical instrument 60 with respect to ultrasound transducer 39 and therefore also with respect to the ultrasound beam generated thereby.

Several exemplary embodiments of device 62 are described hereinbelow. Each of which readily enables the surgeon to align the medical instrument employed with the ultrasound transducer and therefore also with the beam generated thereby. By inserting the medical instrument coaxially with its alignment, the surgeon ensures that the medical instrument is moved on the plane in which the ultrasound beam resides and therefore, eventually the instrument will be visualized in the ultrasound image obtained. This procedure assists the surgeon in bringing the medical instrument "inside" or "into" the ultrasound beam. Device 62 is typically connected to a distal end 68 of transducer 39 via a suitable connector, generally marked as 64. However, direct connection, and connection to other locations on apparatus 20 are also envisaged.

Connector 64 is preferably equipped with wings 65, being aligned within the plane of the ultrasound beam. To this end, distal end 68 of transducer 39, is asymmetrically formed, such that when connector 64 is applied thereon, wings 65 acquire their respective positions.

Figure 5:
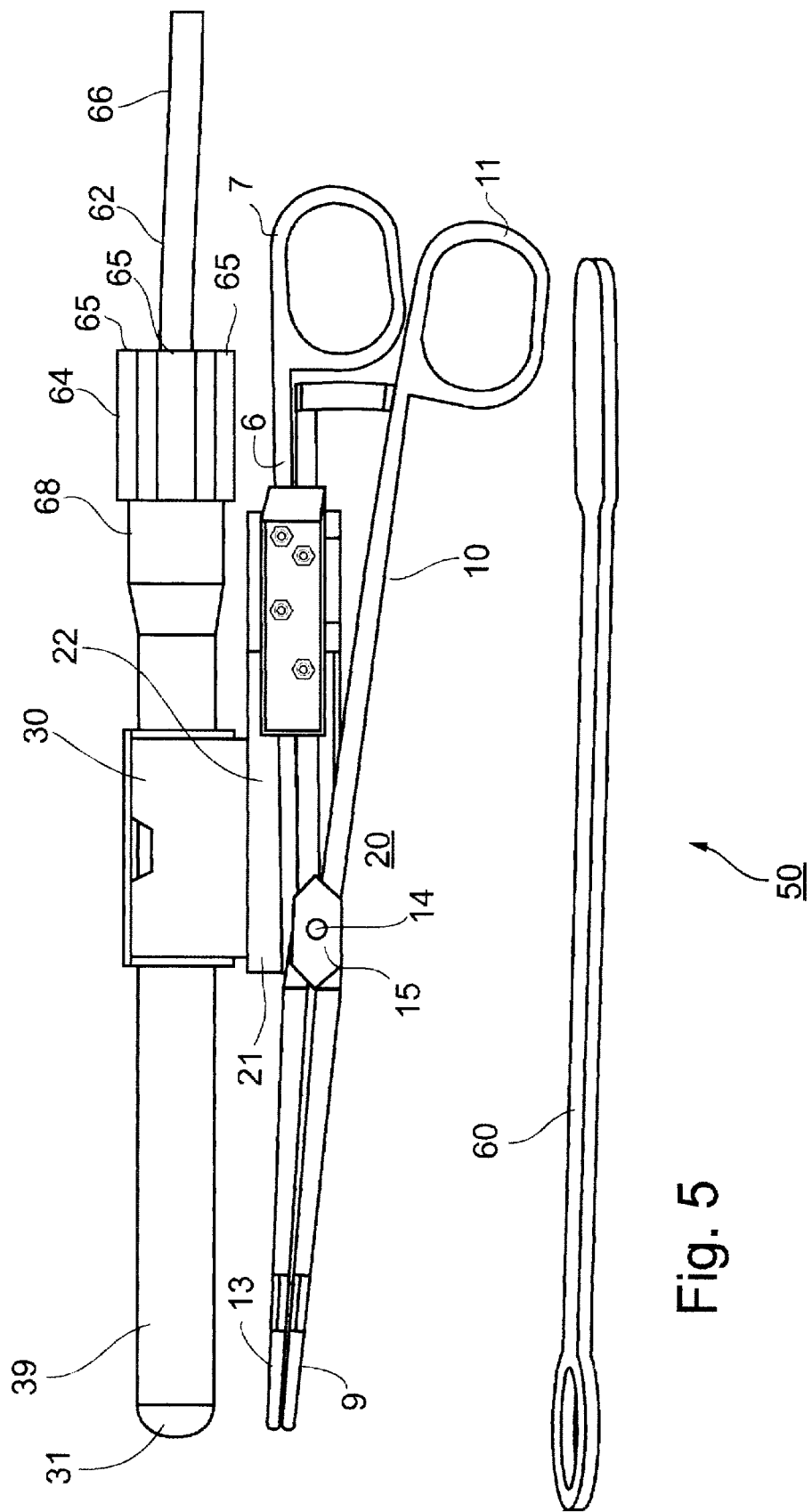
FIGS. 5–8 are schematic illustrations of alternative embodiments of a system according to the present invention including the apparatus shown in FIGS. 4a–b, a medical instrument and a device for monitoring the alignment of the medical instrument with respect to the ultrasound transducer and therefore also with respect to the ultrasound beam.

As specifically shown in FIG. 5, and according to one embodiment, device 62 includes an extension 66 coaxially connected at a distal end 68 of ultrasound transducer 39, thereby facilitating visual alignment of medical instrument 60 with respect to ultrasound transducer 39 and therefore also with respect to the ultrasound beam generated thereby.

According to this embodiment, while inserting medical instrument 60 through the cervix of the patient, the surgeon ensures that instrument 60 is positioned parallel to extension 66, to thereby direct instrument 60 "inside" or "into" the ultrasound beam.

Figure 6:
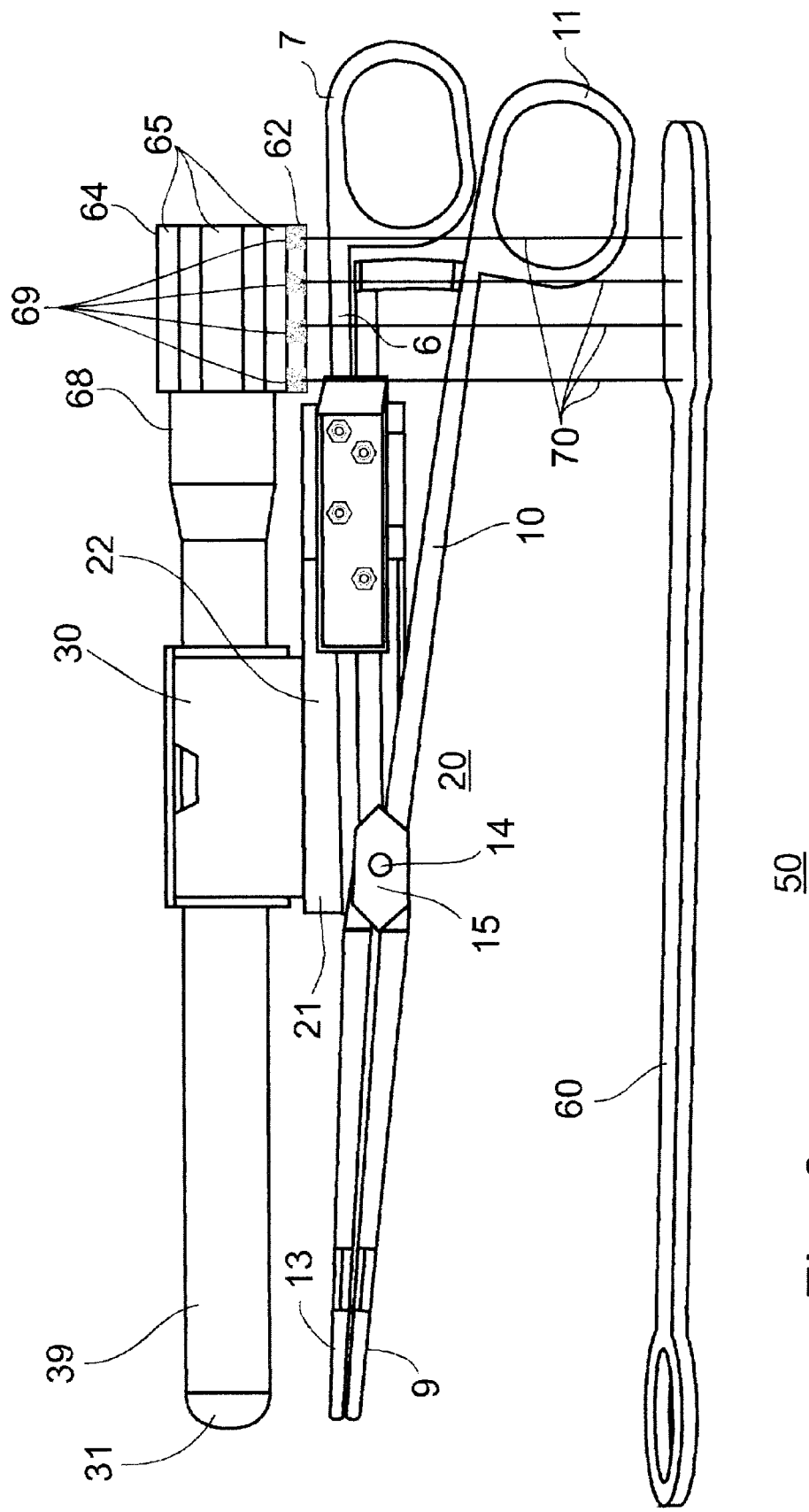

As specifically shown in FIG. 6, and according to yet another embodiment of the present invention, device 62 includes at least one light beam generator 69 (four are shown) connected to apparatus 20, preferably to transducer 39 thereof, preferably via connector 64. Light beam generators 69 serve for generating at least one focused light beam 70. Light beams 70 are projected perpendicular to the plane defined by the ultrasound beam of transducer 39.

Light beams 70 impinging on medical instrument 60, serve for facilitating visual alignment of medical instrument with respect to endovaginal ultrasound transducer 39 and therefore also with respect to the ultrasound beam.

Each of light beam generators 68 may be, for example, a laser source, generating, for example, a green laser beam, which is known not to be absorbed by living tissues. However, non-coherent light sources are also applicable.

According to this embodiment of the invention, while inserting medical instrument 60 through the cervix of the patient, the surgeon ensures that light beams 70 impinge on instrument 60, to thereby direct instrument 60 "inside" or "into" the ultrasound beam of transducer 39. Light beam generators 68 preferably receive energy from a power source, e.g., a battery, implemented in a battery housing located within connector 64.

Each of generators 68 may be, for example, a pointer type laser diode, having, for example, a maximum output below 5 mW, wavelength of 650 nm, with beam dimensions of about 3.0 nm×2.5 nm. A suitable diode is the "ES smallest laser pointer" Cat. No. D53,050 which is available from Edmund Scientific, Industrial Optics Division, Barrington, N.J. 08007-1380 U.S.A. Generators 68 may alternatively be selected to generate a stripe of light. Edmund Scientific Cat. No. D52,562 "Gamma-x laser light show".

Each of generators 68 preferably further includes a beam splitter, e.g., a TECH SPEC pellicle beam splitter. The pellicles are very thin nitrocellulose membranes bonded to lapped aluminum frames. Ghost images are eliminated by the thinness of the membrane as the second surface reflection superimposed on the first surface reflection. The uncoated pellicle reflects 8% and transmits 92% through the visible and near infrared regions. The pellicles' thickness is in the range of 2 μm, their index of reflection is (Nd):1.5. Suitable pellicles are available from Edmund Scientific, Industrial Optics Division, Barrington, N.J. 08007-1380 U.S.A., Cat. No. D39,478).

Figure 7:
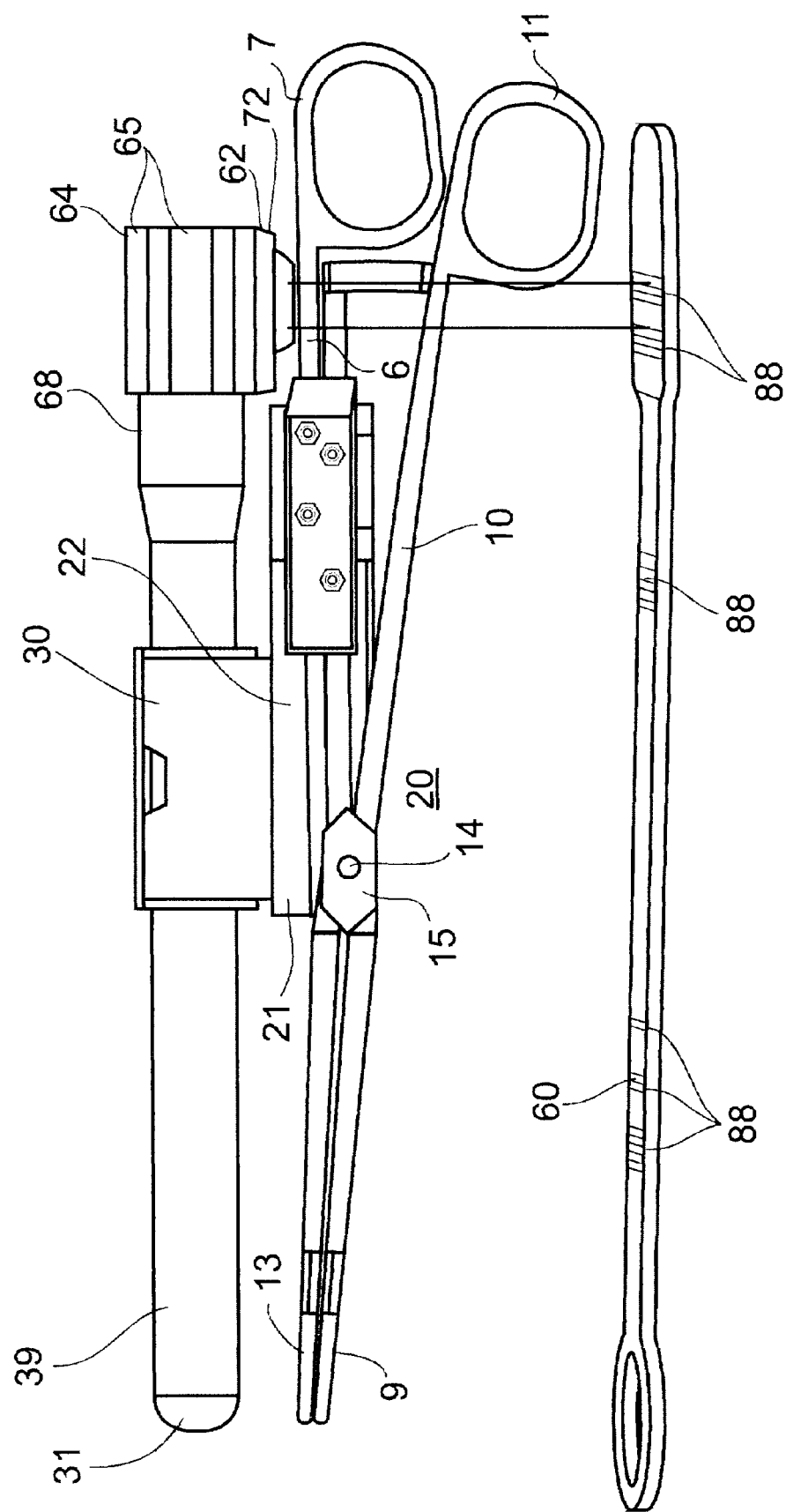

As specifically shown in FIG. 7, and according to still another embodiment of the present invention, device 62 includes an imaging implement 72 connected to apparatus 20, preferably to transducer 39 thereof, preferably via connector 64. Imaging implement 72 serves for generating an image of objects in the plane defined by the ultrasound beam. Implement 72 thereby serves for facilitating alignment of medical instrument 60 with respect to endovaginal ultrasound transducer 39 and therefore also with respect to the ultrasound beam generated thereby. According to this embodiment, while inserting medical instrument 60 through the cervix of the patient, the surgeon ensures that imaging implement 72 "sees" or "captures" instrument 60, to thereby direct instrument 60 "inside" or "into" the ultrasound beam. The image generated by implement 72 is preferably displayed on a screen. A single screen may serve for presenting, in real time, the image perceived through imaging implement 72 superimposed on top of the ultrasound image perceived through transducer 39 such that a relative positioning can be assessed and used to guide medical instrument 60 accordingly.

Implement 72 is positioned such that when an image showing instrument 60 in, for example, a vertical alignment with respect to the screen then the surgeon knows that medical instrument 60 is aligned with respect to endovaginal ultrasound transducer 39 and therefore also with respect to the ultrasound beam generated thereby. The screen may further provide a displayed grid or coordinates, such that assessment of the verticality of the image of instrument 60 is facilitated. Implement 72 preferably receive energy from a power source, e.g., a battery, implemented in a battery housing located within connector 64.

According to a preferred embodiment of the present invention imaging implement 72 is a camera, e.g., a charge coupled device (CCD) camera equipped with a lens or optic fibers arrangement, which is adapted to perceive light in the visible range. According to an alternative embodiment of the present invention implement 72 is a camera sensitive to light in the infrared range, i.e., an infrared (thermal) camera, which may similarly include a lens or an optic fibers arrangement. According to yet another preferred embodiment of the invention imaging implement 72 is an ultrasound implement. According to yet another preferred embodiment of the present invention imaging implement 72 is an X ray implement. In the latter case, an X rays sensitive plate is provided to perceive the image of instrument 60 thereby. Such plates are well known in the art.

According to each of the imaging embodiments described herein an image of instrument 60 is generated, which image enables the surgeon to direct instrument 60 "inside" or "into" the beam generated by ultrasound transducer 39.

As further shown in FIG. 7, according to a preferred embodiment of the present invention medical instrument 60 is provided with marks 88 along at least a portion thereof. Marks 88 are selected identifiable by imaging implement 72 of choice and are therefore usable for image recognition analysis, which may be used to estimate the depth to which instrument 60 has been inserted at any given time. Image recognition is well known art and therefore will not be further elaborated upon herein.

The nature of marks 88 must depend on the nature of imaging implement 72 of choice. Thus, if a CCD camera is selected, marks 88 may acquire a color distinguishable from the background color of instrument 60. If an infrared (thermal) camera is selected, marks 88 may be applied, for example, as substances of increased or decreased heat conductivity as compared with the substance from which instrument 60 is made. If ultrasound or X ray implements are selected, marks 88 may be applied, for example, as holes, recessions, protrusions, etc., to render them distinguishable from the background of instrument 60. In each of these cases, marks 88 may be further selected distinguishable from one another in a fashion, e.g., similar to a bar-code, such that image recognition analysis may be applied.

A suitable CCD is a CCD sensitive to light at 0.2 lux, having a S/N ratio greater than 46 dB. The CCD is preferably monochromatic and is capable of sensing an area of 6.4×4.8 mm. The CCD preferably features miniature size e.g., 30×30×60 mm, and low weight, e.g., 120 grams. A CCD corresponding to the above criteria is distributed by Edmund Scientific, Cat No. D39,244.

Figure 8:
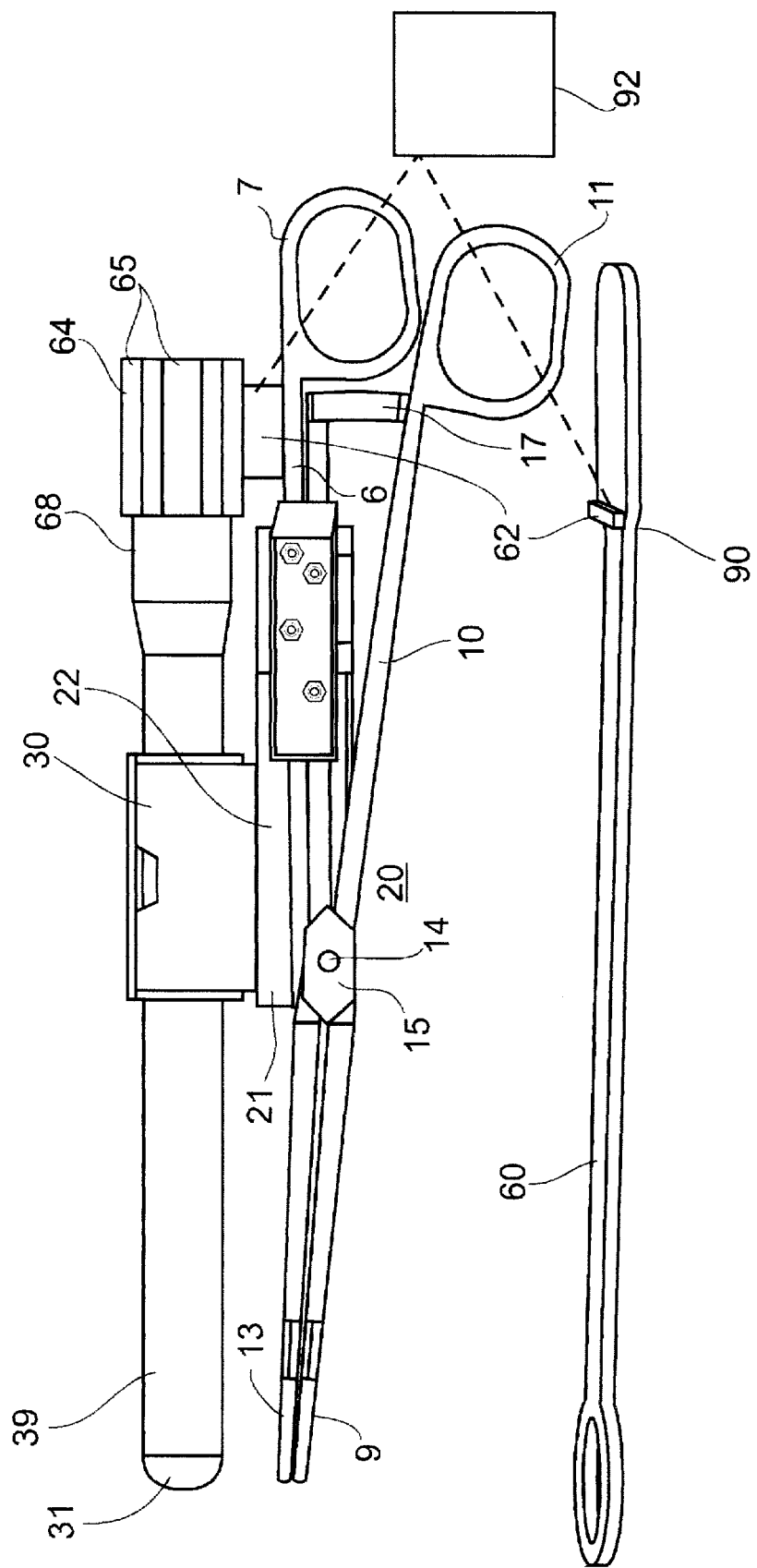

As specifically shown in FIG. 8, according to still another embodiment of the present invention device 62 includes at least two electromagnetic field generators 90 which serve for generating electromagnetic fields. One of electromagnetic field generators 90 is connected to apparatus 20, preferably to transducer 39 thereof, preferably via connector 64. The other electromagnetic field generator 90 is connected to medical instrument 60. According to this embodiment of the present invention, device 62 further includes at least one electromagnetic field sensor, generally indicated by 92. Sensor 92 is positioned in a predetermined position outside the patients body, such that by analyzing the magnetic fields perceived by sensor 92, spatial information of the relative locations of electromagnetic field generators 90 and therefore of transducer 39 and medical instrument 60 is obtainable, thereby facilitating alignment of medical instrument 60 with respect to endovaginal ultrasound transducer 39 and therefore also with respect to the ultrasound beam generated thereby. Further description concerning the operation of electromagnetic field generators and electromagnetic field sensors and the use of sensors to retrieve spatial information from generators is disclosed in, for example, PCT/IL96/00050 (WO 97/03609) and further in U.S. Pat. No. 4,945,305, both are incorporated by reference as if fully set forth herein. Generators 90 are preferably powered by a mutual power source implemented in a dedicated housing in connector 64 or by independent power sources. Suitable power wiring is envisaged.

Further according to the present invention there is provided a method of guiding a medical instrument while monitoring an intra-uterine, cervical or tubal procedures. The method is effected by the following method steps in which in a first step ultrasound transducer 39, mounted within apparatus 20 of system 50 is inserted into a portion of the patient's vagina and ultrasound transducer 39 is fixed against a tissue portion of the patient's vagina or cervix via forceps 5. Alternatively, holder portions 30 and 22 of apparatus 20 are inserted and positioned within the vagina of a patient via forceps 5, following which ultrasound transducer 39 is attached holder 30 and appropriately positioned.

In a second step of the method according to the present invention, a medical instrument 60 is inserted through the cervix and aligned with respect to ultrasound transducer 39 and therefore also with respect to an ultrasound beam produced thereby. Thus, system 50 according to the present invention allows to monitor through the course of the intra-uterine, cervical or tubal procedure, a position of medical instrument 60.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A forceps useful in intrabody positioning of a medical instrument or a device, the forceps comprising:
   (a) a first arm including a first finger holding portion, a first pivot portion and a first tissue holding portion; and
   (b) a second arm including a second finger holding portion, a second pivot portion and a second tissue holding portion; said pivot portion being attached to said second pivot portion so as to form a pivot point about which said first and said second arms co-rotate in a scissor-like motion from a grasping position to an open position and vice-versa,
   wherein, in the grasping position of the forceps,
      (i) said tissue holding portion of the second arm on one side of said pivot point is substantially parallel to the tissue holding portion of said first arm on the corresponding side of said pivot point;
      (ii) said finger holding portion of said second arm on the other side of said pivot point forms an obtuse angle with respect to said tissue holding portion of the second arm; and
      (iii) said finger holding portions of the first and second arms terminate in finger-receiving elements which are both located on one side of the first arm and are aligned with each other in the direction of the scissor-like motion.

2. The forceps of claim 1, wherein said first and said second tissue holding portions are adapted for grasping a cervical tissue.

3. An apparatus for guidance and monitoring of intra-uterine, cervical and tubal procedures, the apparatus comprising an assembly, including:
   (a) an endovaginal ultrasound transducer being adapted for insertion into a portion of a patient's vagina so as to be positionable against a cervix of the patient;
   (b) a forceps including:
      (i) a first arm including a first finger holding portion, a first pivot portion and a first tissue holding portion; and (ii) a second arm including a second finger holding portion, a second pivot portion and a second tissue holding portion; wherein said first pivot portion is attached to said second pivot portion so as to form a pivot point about which said first and said second arms co-rotate in a scissor-like motion from a grasping position to an open position and vice-versa, whereas said first and said second finger holding portions are positioned on one side of a plane defined by a length of said first arm, said plane is perpendicular to said scissor-like motion; and (c) a connector for interconnecting said ultrasound transducer and said forceps, said connector being constructed so as to enable counter resisted movement of said ultrasound transducer relative to said forceps, said counter resisted movement being in a direction away from the cervix.

4. The apparatus of claim 3, wherein said connector includes:
  (i) a forceps portion being attachable to said forceps; and
  (ii) an ultrasound holder portion being attachable to said forceps portion, said ultrasound holder portion including a body and an ultrasound acceptor being for holding said ultrasound transducer, said acceptor is connected to said body of said ultrasound holder portion in a manner so as to allow counter resisted movement of said acceptor relative to said body of said ultrasound holder portion.

5. The apparatus of claim 4, wherein said ultrasound holder portion further includes a spring element interposed between said acceptor and said body such that said counter resisted movement of said acceptor relative to said body in a direction opposite to the patients cervix is counter resisted by said spring element.

6. The apparatus of claim 5, wherein said forceps includes an element attached to, or integrally formed with said first arm, said element being for engaging said forceps portion of said connector.

7. The apparatus of claim 4, wherein said ultrasound holder portion further includes an ultrasound adapter element positioned within said acceptor for firmly holding said ultrasound transducer within said acceptor.

8. The apparatus of claim 4, wherein said ultrasound holder portion of said connector is constructed so as to detach from said forceps portion upon an application of a force of a predetermined magnitude to said endovaginal ultrasound transducer along a longitudinal axis thereof.

9. The apparatus of claim 3, wherein, in the grasping position of the forceps,
  (i) said tissue holding portion of the second arm on one side of said pivot point is substantially parallel to the tissue holding portion of said first arm on the corresponding side of said pivot point;
  (ii) said finger holding portion of said second arm on the other side of said pivot point forms an obtuse angle with respect to said tissue holding portion of the second arm; and
  (iii) said finger holding portions of the first and second arms terminate in finger-receiving elements which are both located on one side of the first arm and are aligned with each other in the direction of the scissor-like motion.

10. A system for guidance and monitoring of a medical instrument utilized in intra-uterine, cervical and tubal procedures, the system comprising:
  (a) an endovaginal ultrasound transducer being adapted for insertion into a portion of a patient's vagina;

(b) a forceps including:
  (i) a first arm including a first finger holding portion, a first pivot portion and a first tissue holding portion; and
  (ii) a second arm including a second finger holding portion, a second pivot portion and a second tissue holding portion; wherein said first pivot portion is attached to said second pivot portion so as to form a pivot point about which said first and said second arms co-rotate in a scissor-like motion from a grasping position to an open position and vice-versa, whereas said first and said second finger holding portions are positioned on one side of a plane defined by a length of said first arm, said plane is perpendicular to said scissor-like motion;

(c) a connector for interconnecting said ultrasound transducer and said forceps, said connector being constructed so as to enable counter resisted movement of said ultrasound transducer relative to said forceps, said movement being in a direction away from the cervix of the patient; and (d) a device for monitoring an alignment of a medical instrument with respect to an ultrasonic beam produced by said endovaginal ultrasound transducer.

11. The system of claim 10, wherein said connector includes:
  (i) a forceps portion being attachable to said forceps; and
  (ii) an ultrasound holder portion being attachable to said forceps portion, said ultrasound holder portion including a body and an ultrasound acceptor being for holding said ultrasound transducer, said acceptor is connected to said body in a manner so as to allow counter resisted movement of said acceptor relative to said body along a longitudinal axis of said ultrasound transducer.

12. The system of claim 11, wherein said forceps includes an element attached to, or integrally formed with said first arm, said element being for engaging said forceps portion of said connector.

13. The system of claim 10, wherein said ultrasound holder portion further includes a spring element interposed between said acceptor and said body such that said counter resisted movement of said acceptor relative to said body in a direction opposite to the patients cervix is counter resisted by said spring element.

14. The system of claim 10, wherein said ultrasound holder portion further includes an ultrasound adapter element positioned within said acceptor for firmly holding said ultrasound transducer within said acceptor.

15. The system of claim 10, wherein said ultrasound holder portion of said connector is constructed so as to detach from said forceps portion upon an application of a force of a predetermined magnitude to said endovaginal ultrasound transducer along a longitudinal axis thereof.

16. The system of claim 10, wherein said device includes an extension coaxially connected at a distal end of said endovaginal ultrasound transducer thereby facilitating visual alignment of said medical instrument with respect to said endovaginal ultrasound transducer and therefore also with respect to said ultrasonic beam.

17. The system of claim 10, wherein said device includes at least one light beam generator connected either to said connector, to said ultrasound transducer or to said forceps, said light beam generator being for generating at least one light beam substantially in a plane defined by said ultrasound beam, said at least one light beam, when impinges on said medical instrument serves for facilitating visual alignment of said medical instrument with respect to said endovaginal ultrasound transducer and therefore also with respect to said ultrasound beam.

18. The system of claim 10, wherein said device is an imaging device connected to said endovaginal ultrasound transducer, said imaging device being for generating an image of said medical instrument superimposable on a plane defined by said ultrasound beam, thereby facilitating alignment of said medical instrument with respect to said endovaginal ultrasound transducer and therefore also with respect to said ultrasound beam.

19. The system of claim 18, wherein said image is displayed on a screen.

20. The system of claim 18, wherein said imaging device includes a camera.

21. The system of claim 20, wherein said camera is sensitive to light in the visible range.

22. The system of claim 20, wherein said camera is an infrared camera.

23. The system of claim 18, wherein said imaging device includes an ultrasound generator.

24. The system of claim 18, wherein said medical instrument is provided with marks along at least a portion thereof, said marks are identifiable by said imaging device and are therefore usable for image recognition analysis.

25. The system of claim 10, wherein said device includes at least two electromagnetic field generators for generating electromagnetic fields, one of said electromagnetic field generator is connected either to said connector, to said ultrasound transducer or to said forceps, whereas the other electromagnetic field generator is connected to said medical instrument, the device further includes at least one electromagnetic field sensor of a predetermined position, such that by analyzing magnetic fields perceived by said at least one electromagnetic sensor, spatial information of the relative locations of said electromagnetic field generators and therefore of said endovaginal ultrasound transducer and said medical instrument is obtainable, thereby facilitating alignment of said medical instrument with respect to said ultrasound beam.

26. The system of claim 10, wherein said medical instrument is selected from the group consisting of an image transmitting device and a surgical instrument.

27. The system of claim 10, wherein, in the grasping position of the forceps,
   (i) said tissue holding portion of the second arm on one side of said pivot point is substantially parallel to the tissue holding portion of said first arm on the corresponding side of said pivot point;
   (ii) said finger holding portion of said second arm on the other side of said pivot point forms an obtuse angle with respect to said tissue holding portion of the second arm; and
   (iii) said finger holding portions of the first and second arms terminate in finger-receiving elements which are both located on one side of the first arm and are aligned with each other in the direction of the scissor-like motion.

* * * * *